(12) United States Patent
Homsy et al.

(10) Patent No.: US 10,835,713 B2
(45) Date of Patent: Nov. 17, 2020

(54) STEERING CONTROL MECHANISM FOR CATHETER

(71) Applicant: Celyad S.A., Mont-Saint-Guibert (BE)

(72) Inventors: Christian Homsy, Woluwe-Saint Pierre (BE); Jean-Pierre Latere-Dwan'isa, Wavre (BE)

(73) Assignee: CELYAD S.A., Mont-Saint-Guibert (BE)

( * ) Notice: Subject to any disclaimer, the term of this patent is extended or adjusted under 35 U.S.C. 154(b) by 1441 days.

(21) Appl. No.: 14/782,250

(22) PCT Filed: Apr. 8, 2014

(86) PCT No.: PCT/EP2014/057093
§ 371 (c)(1),
(2) Date: Oct. 2, 2015

(87) PCT Pub. No.: WO2014/166968
PCT Pub. Date: Oct. 16, 2014

(65) Prior Publication Data
US 2016/0045710 A1    Feb. 18, 2016

(30) Foreign Application Priority Data

Apr. 8, 2013    (GB) .................................. 1306341.7

(51) Int. Cl.
*A61M 25/01* (2006.01)

(52) U.S. Cl.
CPC .... *A61M 25/0136* (2013.01); *A61M 25/0147* (2013.01)

(58) Field of Classification Search
None
See application file for complete search history.

(56) References Cited

U.S. PATENT DOCUMENTS

| 5,779,669 A | 7/1998 | Haissaguerre et al. |
| 6,059,739 A * | 5/2000 | Baumann .......... A61M 25/0147 600/585 |
| 6,464,645 B1 | 10/2002 | Park et al. |

(Continued)

FOREIGN PATENT DOCUMENTS

| EP | 0980693 A1 | 2/2000 |
| EP | 1323448 A2 | 7/2003 |

(Continued)

OTHER PUBLICATIONS

PCT/ISA/210—International Search Report—dated Sep. 19, 2014 (Issued in Application No. PCT/EP2014/057093).

(Continued)

*Primary Examiner* — Nathan R Price
*Assistant Examiner* — Weng Lee
(74) *Attorney, Agent, or Firm* — Venable LLP; Michele V. Frank

(57) ABSTRACT

This document relates to catheter-based therapeutic apparatus and methods for directing therapy within the body of a subject. This document also encompasses a control handle comprising a steering assembly and a delivery assembly suitable for use in conjunction with the catheter-based therapeutic apparatus to provide steering and fine positional control of the catheter tip.

11 Claims, 5 Drawing Sheets

(56) References Cited

U.S. PATENT DOCUMENTS

| | | | | |
|---|---|---|---|---|
| 7,396,335 | B2* | 7/2008 | Gardeski | A61M 25/0136 600/585 |
| 8,562,568 | B2* | 10/2013 | Datta | A61M 25/0136 604/165.04 |
| 2002/0082584 | A1 | 6/2002 | Roseman et al. | |
| 2002/0143291 | A1* | 10/2002 | Slater | A61M 25/0084 604/95.01 |
| 2008/0319314 | A1 | 12/2008 | Hill et al. | |
| 2009/0270835 | A1* | 10/2009 | Kushner | A61B 17/42 604/515 |
| 2011/0270171 | A1 | 11/2011 | Gardeski et al. | |
| 2011/0282176 | A1 | 11/2011 | Tegg | |
| 2012/0089125 | A1* | 4/2012 | Scheibe | A61M 25/0136 604/523 |
| 2012/0203142 | A1 | 8/2012 | Bedell | |

FOREIGN PATENT DOCUMENTS

| | | |
|---|---|---|
| EP | 0787019 B1 | 2/2004 |
| EP | 2438954 A1 | 4/2012 |
| JP | 2002516729 A | 6/2002 |
| JP | 2008119522 A | 5/2008 |
| WO | WO-97/07848 | 3/1997 |
| WO | WO-01/68178 A1 | 9/2001 |
| WO | WO-02/087676 A2 | 11/2002 |
| WO | WO-2010/125166 | 11/2010 |

OTHER PUBLICATIONS

Heldman et al., "Cell Therapy for Myocardial Infarction: Special Delivery"—Journal of Mol. Cell. Cardiology, vol. 44(3), pp. 473-476. (2008).

Sherman, "Cellular Therapy for Chronic Myocardial Disease: Non-surgical Approaches", Basic Appl Myol., vol. 13(1); pp. 11-14. (2003).

Great Britain Search Report, dated Sep. 30, 2013, Issued in GB Application No. 1306341.7.

* cited by examiner

STEERING CONTROL MECHANISM FOR CATHETER

RELATED APPLICATIONS

This application is a U.S. national phase entry of International Application No. PCT/EP2014/057093, which claims priority to Great Britain Application No. 1306341.7, both of which are incorporated by reference.

FIELD

The present invention relates to the field of steerable tip catheters and devices for their control, in particular, steerable tip catheters and handles for their control for delivering a therapeutic agent into a substrate.

BACKGROUND OF THE INVENTION

Cardiovascular diseases is a leading cause of morbidity and mortality worldwide and in contrast to tissues with high reparative capacity, heart tissue is vulnerable to damage that is irreparable by the normal mechanisms of the body. The prevention and treatment of these diseases are thus a major issue and numerous clinical efforts are being made to improve the care and treatment of cardiac disorders.

Regenerative medicine is one current research method for reducing dysfunction of organs, such as the heart, for example (Sherman, *Cellular Therapy for Chronic Myocardial Disease: Nonsurgical approaches, Basic Appl. Myol.* 13(1) 11-14). This treatment involves the injection of therapeutic solutions directly into the organ through devices such as injection catheters. Heldman et al., Cell Therapy for myocardial infarction: Special delivery, *Journal of Molecular and Cellular Cardiology,* 2008, 44, 473-476, describes several such delivery devices for use in the heart along with their disadvantages listed according to type of injection (epicardiac, endocardiac, intracoronary or intravenous).

Steering and fine positional control of the tip of a delivery device such as an injection catheter is of the utmost importance when it is to be used to direct therapy or deliver a therapeutic agent to a predetermined site within the body of a patient. It is imperative that the operator/user of the apparatus is able to undertake functions such as steering of the device and application of therapy concurrently.

Most existing systems currently available require that steering and application of therapy occur consecutively—i.e. as a first step the functional elements of the tip portion are located at the appropriate site within the body of the subject and then therapy is applied. This two-step approach is particularly limiting in dynamic systems, such as the heart, where the movement of the underlying tissues and vessels can displace the tip and result in incomplete or incorrect delivery of therapy.

To mitigate such effects using prior art devices it has been known for two operators/clinicians to use these devices at the same time thereby adopting an approach of three or four-handed operation. Since most prior art devices are not designed or marketed for use three or four-handed not only is this unwieldy in the operating theatre, but it results in an increased risk of error in a surgical procedure. Where multiple operators of a device are required the likelihood of confusion or misdirection is increased, which leads to an increased burden of training and specialisation for clinicians using such devices.

EP 0787019 B1 relates to a steerable catheter and control handle for use in endocardial treatment of the heart. The handle comprises a rotatable thumbwheel mounted at the distal end of the handle for deflection of a catheter tip.

EP 1323448 A2 describes a control handle for use with a steerable catheter. The handle comprises a rotatable thumbwheel mounted at the distal end of the handle for deflection of a catheter tip.

WO 02/087676 A2 describes a steerable catheter and control handle for use in endocardial mapping and/or ablation procedures. The handle comprises a rotatable thumbwheel mounted perpendicular to the longitudinal axis of the handle for deflection of a catheter tip.

Therefore, there remains a need in the art for a catheter apparatus capable of allowing a lone operator a greater level of integration and control than has been achievable with the therapeutic catheters forming the current state of the art. In particular there is a need for a catheter that can integrate both improved flexure and steerability together with functionality that enables delivery of a pharmaceutical preparation to a desired site within the body of a recipient.

These and other uses, features and advantages of the invention should be apparent to those skilled in the art from the teachings provided herein.

SUMMARY OF THE INVENTION

In its primary aspect the invention provides an apparatus suitable for use as a percutaneous or endoscopic catheter comprising:
  a. an elongate shaft that comprises a proximal end and a distal end, wherein the elongate shaft defines at least one central lumen;
  b. at least one steering member that is located within the at least one central lumen and extends along the elongate shaft from the proximal end to an anchor point at the distal end;
  c. a steering assembly that is located at or near to the proximal end of the elongate shaft; and
  d. a handle that comprises a proximal end and a distal end; wherein the steering assembly is comprised at the distal end of the handle and at least a portion of the steering member passes through the central axis of the steering assembly. Typically the steering member of the apparatus comprises a steering wire that is slidably located within an outer conduit. Suitably, the outer conduit consists of a hypotube. The steering assembly may suitably comprise a mechanism for controlling movement of the outer conduit relative to the steering wire, thereby imparting a bending force to the elongate shaft at its distal end.

The described arrangement places the steering controls at the distal end of the handle and, optionally, opposite to additional controls comprised within the handle, such as pharmaceutical delivery controls. This arrangement is particularly ergonomic allowing the operator to use the apparatus, if desired, in a palm-up configuration with the steering controls seated between thumb and forefinger which provides very fine motor control of the distal end of the elongate shaft. In addition, this arrangement frees the spare hand of the operator to manage and control the deployment of and delivery of any therapeutic compositions as and when appropriate. The arrangement of steering and any additional delivery functionalities at opposing ends of the handle thereby reduces muscle fatigue and advantageously allows for single user (one or two handed) operation rather than cumbersome and awkward two user (four handed) operation.

Suitably, the steering assembly comprises a slidable carriage that is arranged so as to impart force on the outer conduit but not on the steering wire when the carriage is moved axially. Optionally, the steering assembly comprises a slidable carriage that is arranged so as to impart force on the steering wire but not on the outer conduit when the carriage is moved axially. The movement of the carriage may be mediated via engagement with a threaded bar. The rotation of the threaded bar is suitably controlled via a wheel or dial. Typically, the wheel is positioned at the distal end of the handle and the steering assembly is located proximally to the wheel. Alternatively, movement of the carriage can be controlled by a slider arrangement.

The apparatus may suitably further comprise a therapeutic device. Typically, the therapeutic device comprises at least one penetrating member, wherein the penetrating member extends along the elongate shaft from the proximal end to the distal end, and wherein the penetrating member is capable of being advanced in distal direction beyond the distal end of the elongate shaft. The penetrating member suitably comprises a hollow needle.

Suitably, the handle of the apparatus further comprises a delivery assembly, wherein the hollow needle is in fluid communication with the delivery assembly. The delivery assembly may suitably be located at the proximal end of the handle. The handle may be suitably configured such that the delivery assembly and the steering assembly are placed in a substantially linear arrangement along the central axis of the handle. Typically, the delivery assembly is arranged to facilitate delivery of a pharmaceutical composition. Optionally, the delivery assembly is arranged to facilitate delivery of a cellular preparation.

A second aspect of the invention provides a handle, suitable for use in conjunction with a percutaneous or endoscopic therapeutic catheter, the handle comprising:
 a. a housing, wherein the housing is substantially elongate in configuration and comprises a proximal portion and a distal portion;
 b. a steering assembly that is located in the distal portion of the housing, wherein the steering assembly is adapted to cooperate with and control the steering mechanism of a catheter;
 c. a delivery assembly that is located in the proximal portion of the housing, wherein the delivery assembly is adapted to control application of therapy via the catheter;
wherein the handle is configured such that the delivery assembly and the steering assembly are placed in a substantially linear arrangement along the central longitudinal axis of the housing.

Typically, the steering assembly of the handle controls movement of the steering mechanism of the catheter. The steering mechanism suitably comprises a steering wire that is slidably located within an outer conduit, and the steering assembly controls movement of the outer conduit relative to the steering wire, thereby imparting a bending force to catheter that facilitates steering of the catheter when in use.

A third aspect of the invention provides a percutaneous catheter that comprises the afore-mentioned handle.

A fourth aspect of the invention provides an endoscopic catheter that comprises the afore-mentioned handle.

A fifth aspect of the invention provides a method for directing therapy within the body of a subject comprising using the catheter-based therapeutic apparatus of the present invention.

Suitably, the method for directing therapy within the body of a subject comprises a catheter-based therapeutic apparatus that is controlled and maneuvered via the handle of the present invention. Typically, the therapy comprises delivery of a pharmaceutical composition. Optionally, the therapy comprises delivery of a cellular preparation.

BRIEF DESCRIPTION OF THE DRAWINGS

The invention is further illustrated by the accompanying figures in which.

DETAILED DESCRIPTION OF THE INVENTION

Figure 1:
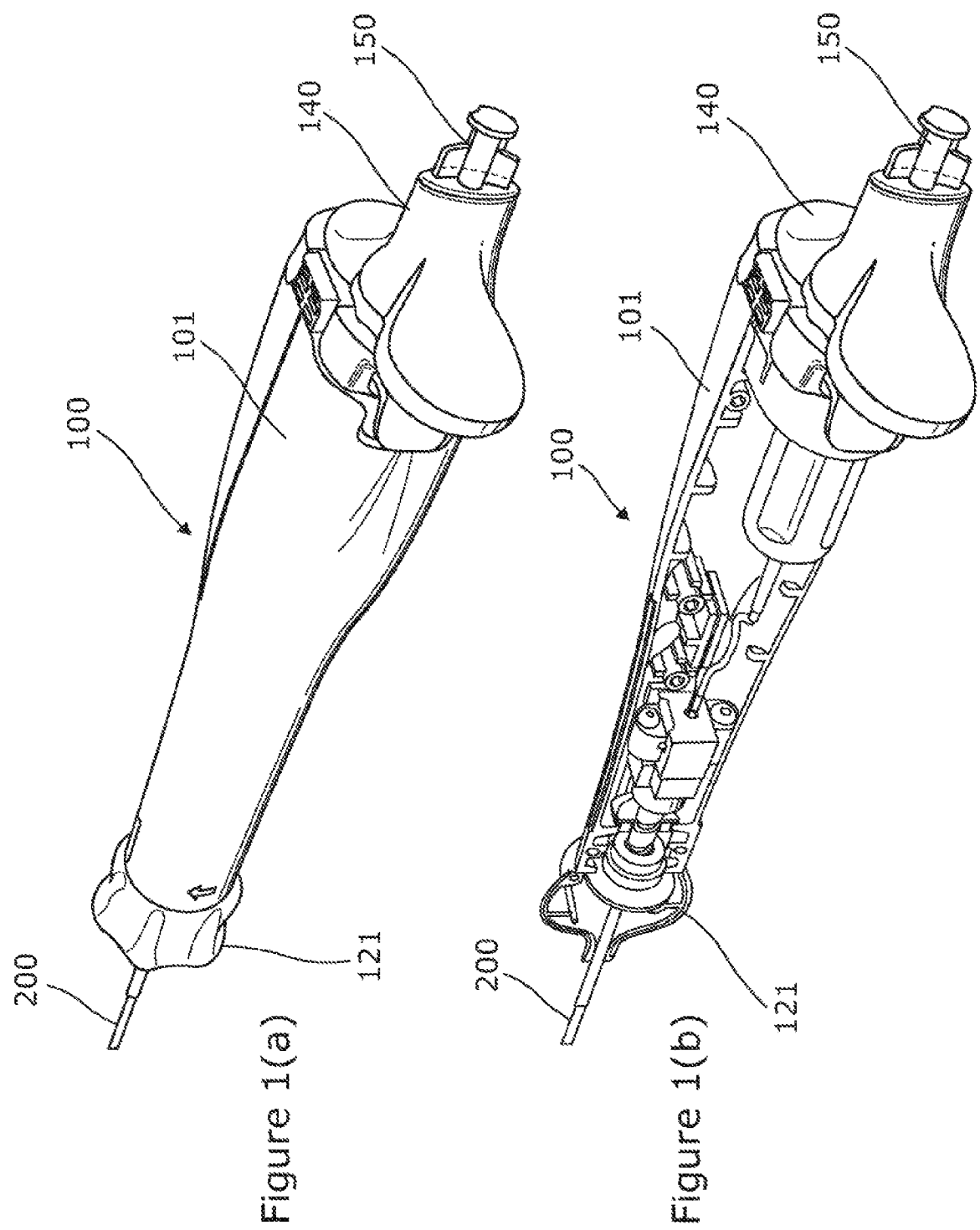
FIG. 1 is an oblique view of the handle assembly of one embodiment of the invention (a) shows an unexploded view of the housing, (b) is exploded so as to show the internal arrangement of the handle assembly.

All references cited herein are incorporated by reference in their entirety. Unless otherwise defined, all technical and scientific terms used herein have the same meaning as commonly understood by one of ordinary skill in the art to which this invention belongs.

The invention provides for a medical device comprising an elongated shaft assembly, typically in the form of a catheter that comprises a functional element at its distal tip and a user interface at the proximal terminus. In the art the user interface is sometimes referred to as a handle, handle assembly or hub.

Prior to setting forth the invention, a number of definitions are provided that will assist in the understanding of the invention. It should be appreciated that the term 'comprising' as used herein is intended to mean including but not limited purely to any accompanying features.

As used herein the terms distal and proximal are used to refer to orientation along the longitudinal axis of the device. Since the devices of the invention are elongate in nature and conform to a single dimension, in use the distal direction refers to the end of the device furthest away from the operator and the proximal direction the end of the device closest to the operator. It should be noted that the term proximal should not be confused with the term 'proximate', which adopts its conventional meaning of 'near to'.

In its broadest configuration the apparatus of the invention comprises an elongate shaft assembly which is attached to a handle assembly. The elongate shaft is suitably configured for percutaneous use, such as via intravascular, endoscopic or laparoscopic modes that involves introduction into a hollow anatomical vessel or duct within the body of a subject animal. The handle assembly remains outside—i.e. external to—the body of the subject. In a specific embodiment of the invention the elongate shaft is a catheter, suitably comprising a tube portion that may define one or more lumens located coaxially within the shaft. The catheter may be adapted for use with an associated guidewire in convention over-the-wire (OTW) or monorail configurations. In embodiments where the catheter is adapted for use with a guidewire, the catheter will further comprise an additional lumen that is adapted to accommodate a guidewire. Any such guidewire may be prelocated within the subject in order to facilitate placement of the device when in use.

The device of the present invention is suitable for intravascular use, in particular intracoronary use. However, in other embodiments of the invention the device may be used within the blood vessels of the abdomen, the head and neck or limbs, or within the ducts of the gastrointestinal or genito-urinary tracts.

In a specific embodiment of the invention the apparatus is configured so as to provide a delivery catheter of the type disclosed in Applicant's International Patent Application published as WO-A-2010/125166, and marketed under the brand names C-CATH® and C-CATH$_{EZ}$® (Cardio3 BioSciences SA, Mont-Saint Guibert, Belgium).

Typically, the apparatus of the invention is operated according to three main phases of therapy: an insertion phase, a therapy phase and a removal phase. The insertion phase includes the intravascular/endoscopic/laparoscopic insertion of the device and the location of the device to the site of treatment where therapy is to be administered. The therapy phase includes administering pharmaceutical compositions or cellular preparations where required. The removal phase includes the withdrawal of the device from the site of treatment; usually back along the initial insertion route. It will be appreciated that the therapy phase may be repeated several times before the removal phase commences.

According to one embodiment of the invention the elongated shaft is provided with a central lumen that extends along its entire length. The elongate shaft of embodiments of the invention are suitably constructed as catheters in a variety of sizes typically ranging from about 0.15 mm up to about 4 mm in diameter (corresponds to French sizes 0.5 to 12). The central lumen provides a conduit which may allow engagement with a prelocated guidewire. Alternatively, the central lumen provides a conduit within which the penetrating member is housed. The central lumen may extend entirely along the shaft such that the distal terminus comprises an aperture allowing fluid communication between the central lumen and the hollow anatomical structure within which the shaft is located. In such embodiments of the invention the penetrating member, when advanced out of the central lumen, may be deployed along a path that is at least in part coaxial with the axis of the central lumen. In an embodiment of the invention, the central lumen is formed from a polymer liner that sits coaxially within the elongate shaft. Suitably the polymer liner is comprised of a material such as a fluoropolymer, for example PTFE. In this embodiment of the invention the distal portion, at least, of the polymer liner may be linked or otherwise fixed to the distal part of the elongate shaft and the main portion of the polymer liner is allowed to move freely within and with respect to the elongate shaft. Advantages of this arrangement are that the flexibility of the shaft is improved and deployment and consistency of the penetrating member is easier to control. Embodiments of the invention permit for location of the central lumen centrally within the body of the elongate shaft or at a position that is radially offset from the central longitudinal axis It will be appreciated that alternative configurations may also be adopted in which the central lumen may be diverted radially at a position proximal to the distal terminus of the elongate shaft. Such configurations permit embodiments of the invention in which the penetrating member is diverted radially outwardly from the device when extended out of the central lumen. In this embodiment of the invention the central lumen will create an aperture in the side of the elongate shaft rather than at its terminus. Where the aperture is located in the side of the elongate shaft but close (proximate) to the distal terminus the region defined by the distal terminus and the adjacent radially located aperture is referred to collectively as the distal tip portion of the elongate shaft. The distal tip portion of the elongate shaft may comprise a radiopaque material or coating so as to facilitate visualisation during surgical procedures when using X-rays. The shaft may further comprise one or more echogenic surfaces to further facilitate use with ultrasound visualisation (e.g. IVUS) technologies.

The penetrating member may be a retractable hollow needle or stylet formed from a suitable material including polyether ether ketone (PEEK), carbon fibre loaded liquid crystalline polymer, tungsten carbide polyimide, stainless steel, gold, platinum, shape memory alloy (including NiTinol) or other suitable surgically compatible metal alloys. Typically, the penetrating member is formed from a radiopaque material so as to facilitate visualisation during surgical procedures when using X-ray guidance. The penetrating member may further comprise one or more echogenic surfaces to further facilitate use with ultrasound visualisation (e.g. IVUS) technologies. The penetrating member is provided with a sharp tip at its distal end, which is used to puncture and penetrate tissue at the site of treatment. The lumen of the penetrating member allows for administration of substances, including cell preparations and pharmaceutical compositions, to the site of treatment through the lumen of the penetrating member. The lumen of the penetrating member may also be used as an aspiration channel to extract fluids from the site of treatment and/or to take a tissue biopsy.

An exemplary device of the invention comprises an elongate shaft which encloses at least one central lumen. The central lumen extends along substantially the entire length of the elongate shaft and provides a conduit for delivery and location of the penetrating member. In one embodiment of the invention, the elongate shaft may also comprise at least one additional lumen located adjacent to the central lumen in a coaxial arrangement. The at least one additional lumen may accommodate one or more steering members. Suitably, the steering member comprises a pull wire that extends along the entire length of the elongate shaft and allows the user to apply a steering action particularly at the distal tip of the elongate shaft via the well-known Bowden cable method of transmitting movement. In a further embodiment of the invention the elongate shaft comprises only a central lumen that accommodates both the penetrating member and one or more adjacent steering members.

The elongate shaft is suitably constructed from a polymeric material such as a silicone rubber or a polymer including thermoplastic elastomer, PEEK, polyimide, high density polyethylene (HDPE), Pebax, and/or nylon; or composites thereof. All or a portion of the shaft may also comprise a low friction or lubricious coating that may, for example, include a fluoropolymer such as a PTFE or parylene.

Steering and fine positional control of the distal tip of the elongate shaft is of particular importance where the apparatus of the invention is to be used to direct therapy or deliver a therapeutic agent to a predetermined site within the body of a subject (e.g. a patient). By "steering" it is meant that the distal tip of the apparatus may be diverted away from the longitudinal axis of the device to an extent as required and controlled by the operator. Steering is also commonly termed within the art "flexure" or "bending". It is imperative that the operator/user of the apparatus is able to undertake functions such as steering of the device and application of therapy as concurrently as possible. Most existing systems currently available require that steering and application of therapy occur in very distinct consecutive phases—i.e. as a first step the functional elements of the distal tip portion are located at the appropriate site within the body of the subject and then therapy is applied. This two-step approach can introduce time delays and is particularly limiting in dynamic systems such as the heart where movement of the underlying tissues and vessels can displace the distal tip portion and result in incomplete or incorrect delivery of therapy. To mitigate such effects using prior art devices it has been known for two operators/clinicians to use these devices at the same time thereby adopting an approach of three or four-handed operation. Since most prior art devices are not designed or marketed for use three or four-handed not only is this unwieldy in the operating theatre, but it results in an increased risk of error in a surgical procedure. It is of particular advantage, therefore, that the apparatus of the present invention is enables a single operator a greater level of integration and control than has been previously achievable.

Steering and fine positional control is mediated via the handle assembly which is located at and integrated with the proximal end of the elongate shaft. FIG. 1(*a*) shows an oblique view of an embodiment of the handle assembly 100, which comprises a housing 101. Located adjacent to and abutting distal end of the housing 101 is a control wheel 121, and at the proximal terminus of the handle is located a therapy delivery member 140. The elongate shaft 200 passes through the control wheel 121 into the housing 101, as is evident in the exploded view of the handle assembly 100 in FIG. 1(*b*).

Figure 3A:
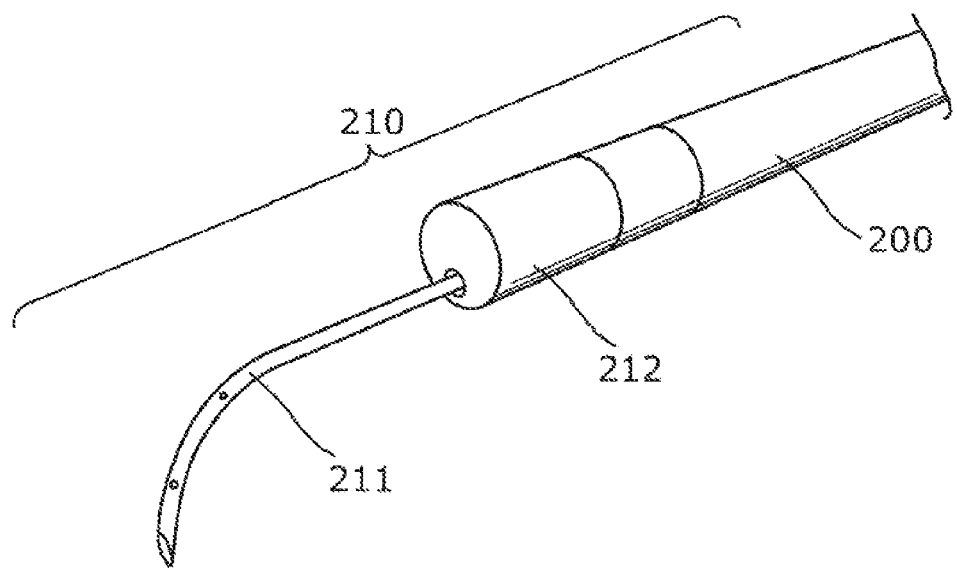
FIG. 3 shows the distal tip portion of an embodiment of the invention with a curved hollow needle in the deployed state, (a) shows the view with a distal stopper piece in place and (b) shows the view with the stopper removed to reveal the steering wire and the central lumen.
Figure 3B:
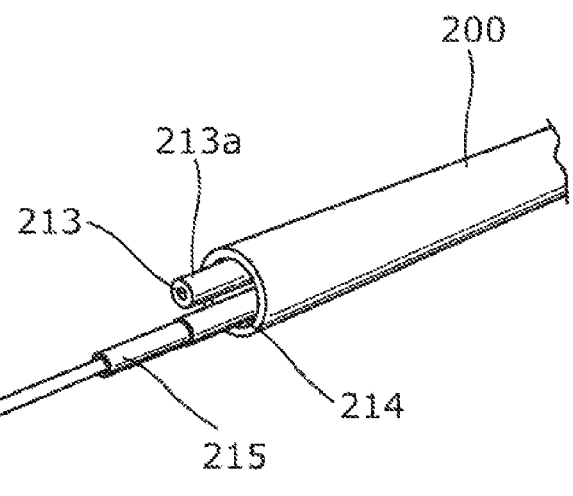

FIGS. 3(*a*) and (*b*) show the distal tip portion 210 of the elongate shaft 200 in one particular configuration of the apparatus of the invention. It will be appreciated that the handle assembly 100 is not limited to control of or use with this particular embodiment of the invention and may be compatible with other arrangements. FIGS. 3(*a*) and (*b*) show a delivery needle 211 in a deployed configuration extended outwardly from the shaft 200. During the insertion phase the needle 211 is stowed within the lumen 214. The needle 211 may be housed within a sheath 215 to facilitate delivery and enable fluid communication between the needle and the delivery member 140 located within the handle assembly 100. The elongate shaft 200 also comprises at least one steering wire 213 which is also located within the lumen 214 and extends along the entire length of the shaft 200. The steering wire 213 is typically comprised within a conduit such as a hypotube 213*a* that allows for slidable movement of the wire 213 relative to the hypotube 213*a*. The hypotube 213*a* may be fabricated from a metal, such as stainless steel, or from a any other material featured with similar rigidity. The distal end of the hypotube 213*a* is rigidly connected to the distal end of the elongate shaft 200 at a point or plurality of points proximal to the region to be steered/flexed The distal terminus of the lumen 214 is enclosed by a stopper 212 which provides an anchor point for the distal end of the steering wire 213. The stopper 212 comprises at least one aperture to allow passage of the needle 211 therethrough upon deployment.

Figure 2:
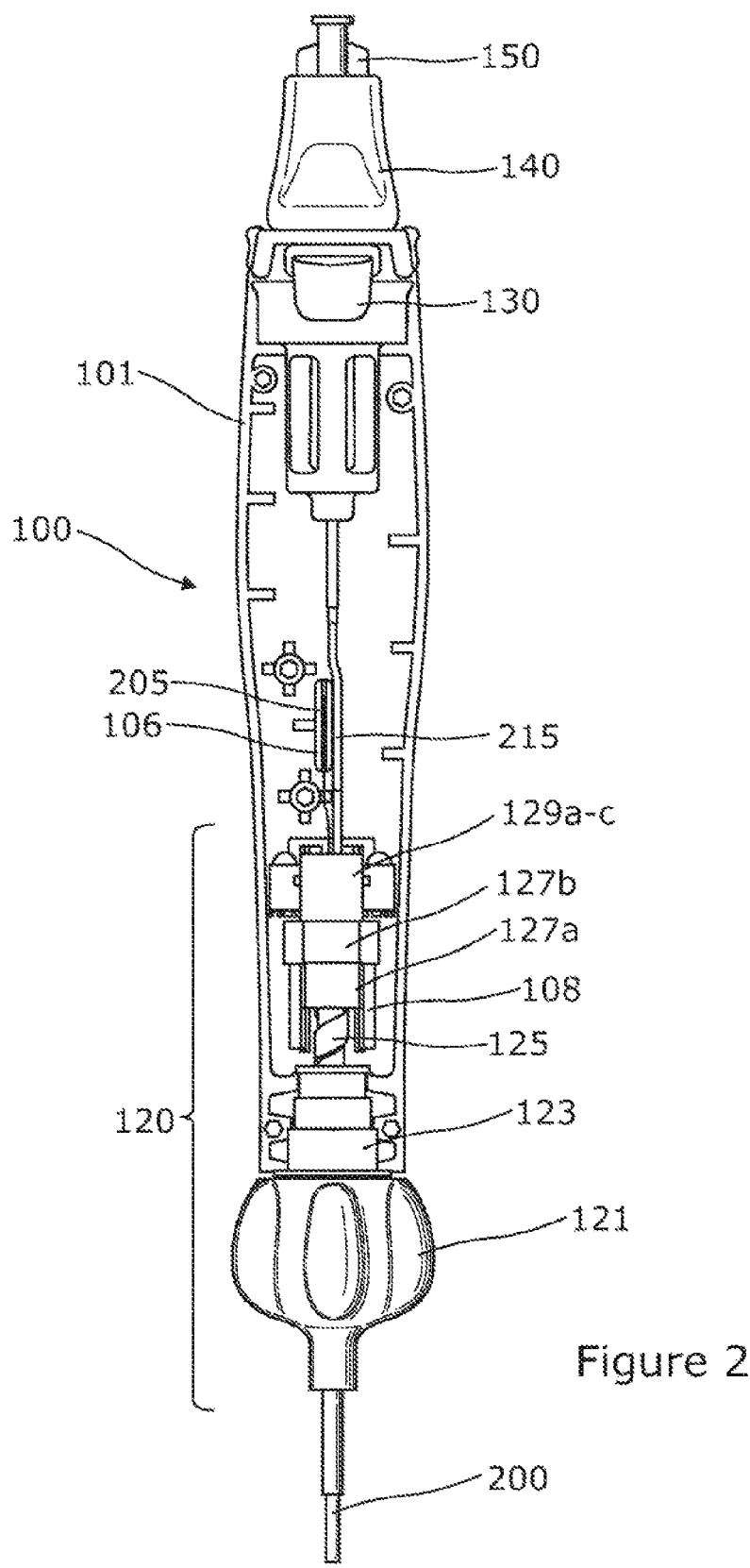
FIG. 2 is a side sectional view of the handle assembly of FIG. 1, the axis of the handle assembly is shown with distal at the bottom and proximal at the top of the figure.

A side sectional view of the handle assembly 100 is shown in FIG. 2. The elongate shaft 200 passes along the central axis of the assembly 100 into the housing 101. The proximal terminus of the shaft 200 is located in the distal end of the housing 101 within a steering mechanism 120, which is described in more detail below.

In the embodiment shown, the steering wire 213 extends beyond the steering assembly 120 and is rigidly fixed at its proximal end to the body of the housing 101. In an alternative embodiment (not shown), the proximal end of the steering wire 213 is rigidly fixed to a member which is axially slideable relative to the handle assembly 100. In this embodiment, the steering assembly is rigidly fixed to the body of the housing whilst the steering wire 213 is axially movable relative to the steering assembly.

The sheath 215 also extends beyond the steering mechanism 120 towards the proximal end of the housing 101 where it engages with the delivery mechanism 130. The delivery mechanism 130 comprises a delivery member 140 that controls deployment of the needle 211 through a user operated push-pull plunger arrangement. Located coaxially with the delivery member 140 is means for connecting a therapy administration device 150 that may be suitably in the form of a piston, syringe or dosage pump that is in fluid communication with the lumen of the sheath 215 and, thus, the hollow needle 211. The connector 150 for the administration device is operated by the user to introduce, for example, a therapeutic composition into the lumen of the needle 211 and consequently into the subject at the site of therapy. The connector 150 may comprise one or more ports (e.g. a Luer Lock) to facilitate loading of a therapeutic composition into the device, either before or during the therapeutic procedure.

Figure 4:
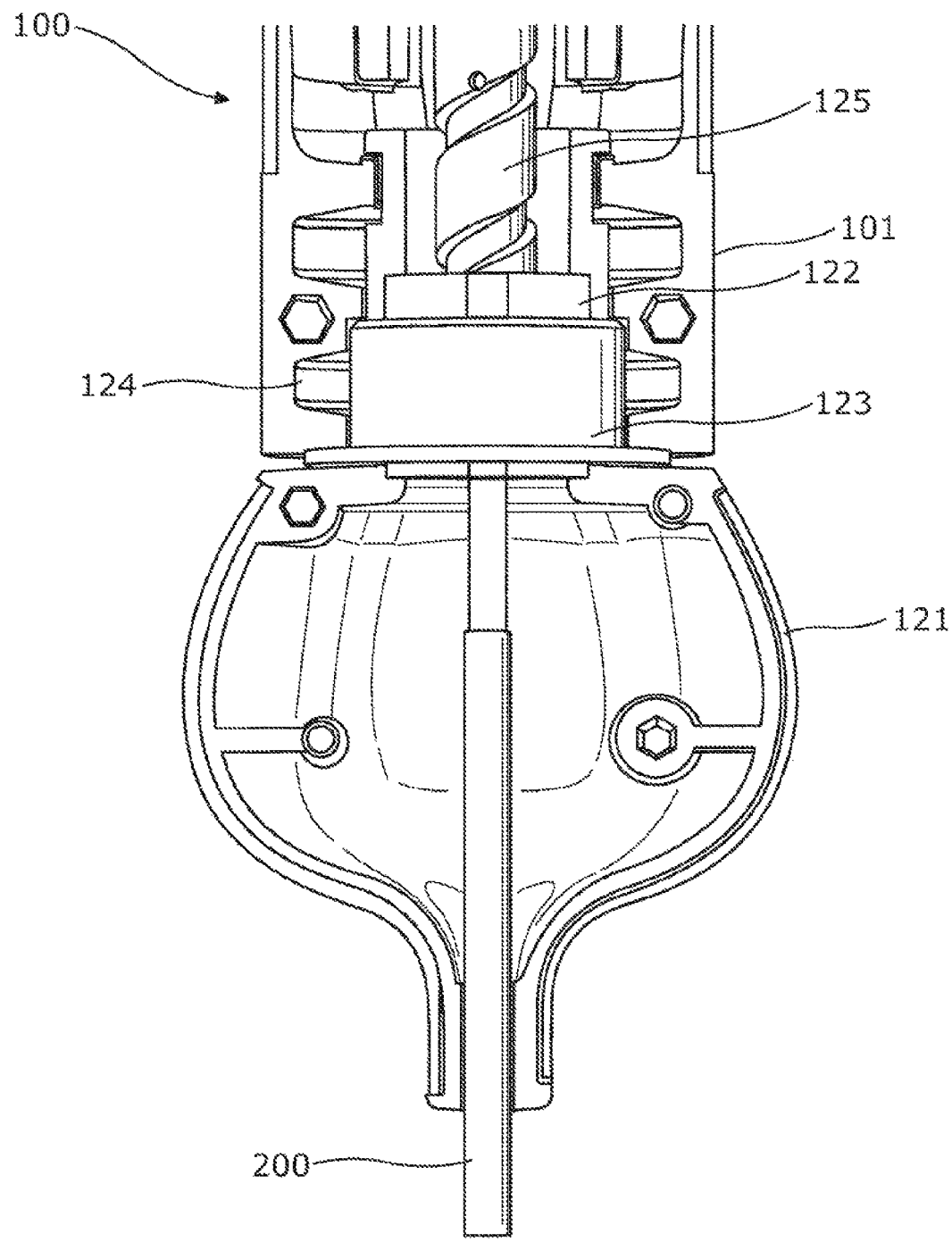
FIG. 4 is a side sectional view of the control wheel assembly at the distal end of the handle.

The steering mechanism 120 of the handle 100 is located at the distal end of the housing 101. Steering/flexure of the distal end is achieved by axial movement of the elongate shaft 200/hypotube 213*a* relative to the steering wire 213. In the embodiment shown, this axial movement is achieved through rotation of the control wheel 121 which in turn is translated into axial movement via a threaded bar 125. FIG. 4 shows a sectional view of the control wheel 121 with the elongate shaft 200 passing along the central axis. In the embodiment shown in FIG. 4, the control wheel is formed from two symmetrical plastic pieces that in combination form a bulb shaped component. It will be understood, however, that alternative configurations of the control wheel 121 may be contemplated by the skilled addressee and may include use of a slider arrangement or a lever to impart control of movement. The control wheel 121 is rotatable about the elongate shaft 200 in both clockwise and anti-clockwise directions. The proximal end of control wheel 121 is formed into a moulding that sits within recess 124 at the distal end of the housing 101. The moulding comprises a plurality of surfaces that enable a secure engagement between the control wheel 121 and the recess 124 but still permit the control wheel 121 to rotate freely. The rotation of the control wheel is further facilitated by the presence of a bushing 123 that forms a slidable surface around the distal entrance to the recess 124 in which the control wheel 121 is seated. The interior surface of the control wheel 121 comprises a recess into which is located a nut 122. The nut 122 is fixed to the control wheel 121 such that rotation of the control wheel controls rotation of the nut 122. The proximal end of the nut 122 is linked to a hollow threaded bar 125 that extends proximally to a point where it abuts a termination disk 128. The termination disk is comprised within carriage assembly 126 that is threaded onto the bar 125 and runs along rails 108 formed on the interior surface of the housing 101. The termination disk 128 sits between proximal and distal carriage components 129a-b which are held together by screws 129c.

Figure 5:
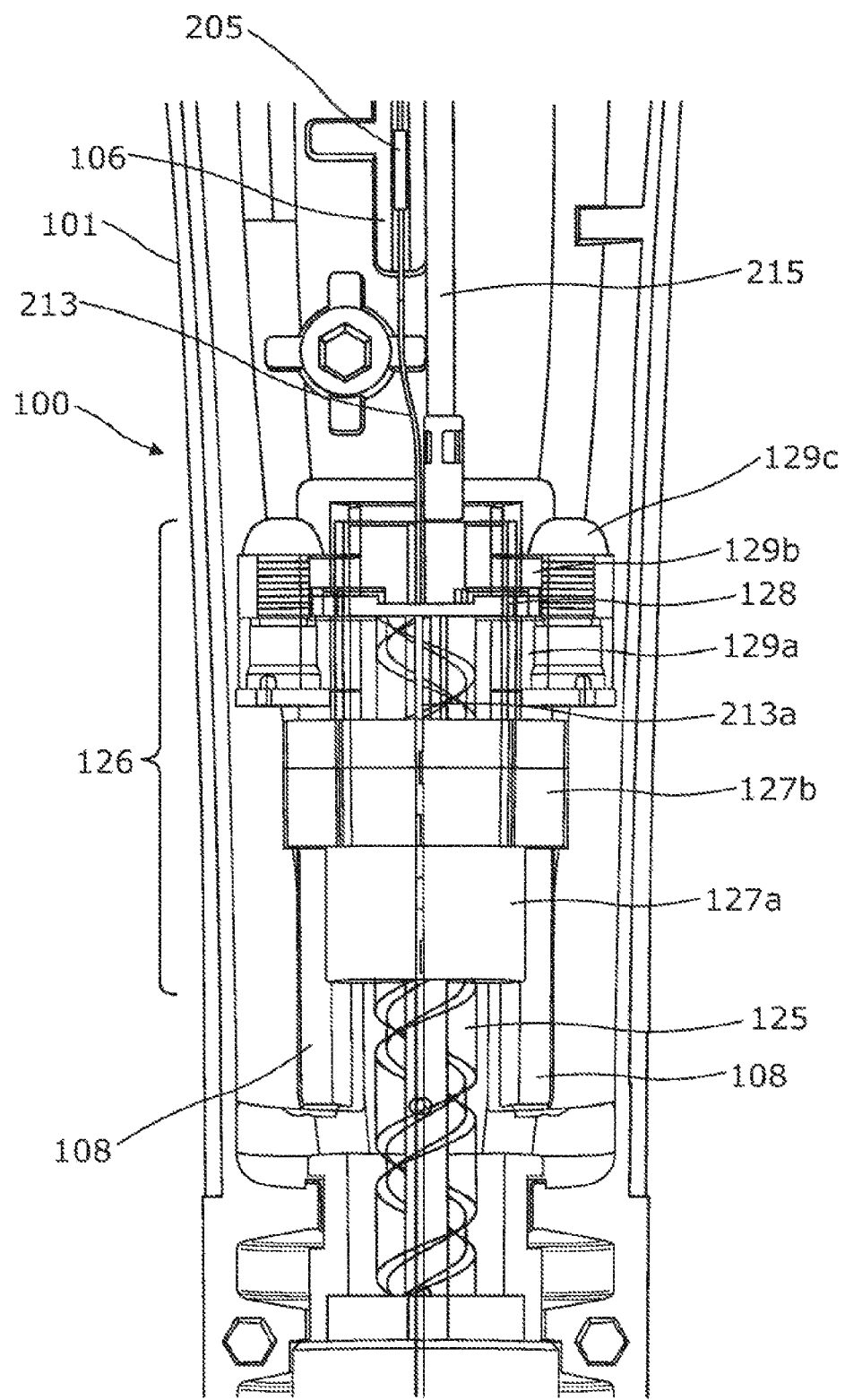
FIG. 5 shows close up sectional view of the steering assembly and in particular the carriage arrangement according to one embodiment of the invention.

As can be seen in FIG. 5, the sheath 215 and the steering wire 213 extend along the lumen of the hollow bar 125 to a point proximal to the termination disk 128 at which point they diverge as described above. However, the hypotube 213a of the steering wire 213 terminates flush with the proximal face of the termination disk 128 such that during advancement of the carriage 126 force is translated from the proximal to the distal end of the hypotube 213a. This prevents the region of the elongate sheath 200 between these two points from flexing during steering. The carriage assembly comprises a limiter nut 127a and spacer 127b at the distal end in order to limit the extent of movement of the carriage assembly 126 along the bar 125.

In use, the operator of the device is able to control steering of the distal tip 210 via rotation of the control wheel 121, the movement of which is transmitted to the threaded bar 125 and, thus, to the carriage assembly 126. Hence, rotational movement of the control wheel 121 is converted to translational movement of the carriage assembly 126 along the axis of the handle 100. As the carriage assembly 126 moves along the rails 108 in a distal direction in response to rotation of the control wheel 121, the termination disk 128 is brought to bear upon the hypotube 213a causing relative movement of the steering wire 213 to the hypotube 213a. By virtue of the foreshortening effect that is caused the movement is transmitted to the fixing point between the steering wire 213 and the stopper 212 in the distal tip 210 of the elongate sheath 200. In this way, small rotational movements of the control wheel 121 result in movement of the tip 210 in a highly controlled manner. The present arrangement allows for the distal tip 210 to be diverted (i.e. curled) by an angle of in excess of 180°, typically over 230°. Overall rotation of the elongate sheath 200 is achieved by rotation of the handle 100 as a whole about the longitudinal axis of the device.

The described arrangement places the steering controls at the distal end of the handle 100 and opposite to the delivery controls. This arrangement is particularly ergonomic allowing the operator to use the apparatus, if desired, in a palm-up configuration with the control wheel 121 seated between thumb and forefinger which provides very fine motor control of the distal tip 210. In addition, this arrangement frees the spare hand of the operator to manage and control the deployment of the needle 211 and delivery of therapeutic compositions as and when appropriate. The arrangement of steering and delivery functionalities at opposing ends of the handle 100 thereby reduces muscle fatigue associated with prior art handles and advantageously allows for single user (two handed) operation rather than cumbersome and awkward two user (three or four handed) operation.

The steering and handle assembly as currently described is not limited to use in delivery catheters. It will be appreciated by the skilled person that the handle assembly can be adapted for use in any catheter, endoscope or laparoscope that requires operator execution of fine control and steering ability over the distal tip region. Hence, it is appropriate for the handle of the invention to be adapted for use with ablation catheters (e.g. radiofrequency, irreversible electroporation or laser ablation catheter devices), medical imaging catheters (e.g. IVUS or other ultrasound imaging catheters), dilation catheters (e.g. balloon dilation angioplasty or stent delivery catheters). In non-delivery catheter arrangements the delivery assembly 140 is simply replaced with the desired appropriate control mechanism to match with the altered functional configuration at the distal tip 210.

By way of non-limiting example, if the steering assembly is to be used in conjunction with a balloon dilation angioplasty catheter, the controls for deploying the expandable balloon would be located at the proximal end of the handle with the steering assembly as described above located at the distal end of the handle.

It should be understood that the different embodiments of the invention described herein can be combined where appropriate and that features of the embodiments of the invention can be used interchangeably with other embodiments where appropriate.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the scope of the invention as defined by the claims.

What is claimed is:

1. An apparatus, suitable for use as a percutaneous or endoscopic catheter, the apparatus comprising:
    a. an elongate shaft that comprises a proximal end and a distal end, wherein the elongate shaft defines at least one central lumen;
    b. at least one steering member that is located within the at least one central lumen and extends along the elongate shaft from the proximal end to an anchor point at the distal end, wherein the steering member comprises:
        i. a steering wire that is slidably located within an outer conduit, and
        ii. a mechanism for controlling movement of the outer conduit relative to the steering wire, thereby allowing a bending force to be applied to the elongate shaft at its distal end;
    c. a steering assembly that is located at or near to the proximal end of the elongate shaft, wherein the steering assembly comprises a slidable carriage that is arranged so as to impart force on the outer conduit but not on the steering wire when the carriage is moved axially; and
    d. a handle that comprises a proximal end and a distal end;
    wherein the steering assembly is comprised at the distal end of the handle and at least a portion of the steering member passes through a central axis of the steering assembly;
    wherein the apparatus further comprises a therapeutic device, wherein the therapeutic device comprises at least one penetrating member, wherein the penetrating member extends along the elongate shaft from the proximal end to the distal end, wherein the penetrating member comprises a hollow needle, and wherein the penetrating member is capable of being advanced in a distal direction from a stowed state where the penetrating member is housed within the central lumen to a deployed state where the penetrating member is advanced out of the central lumen beyond the distal end of the elongate shaft.

2. The apparatus of claim 1, wherein the outer conduit consists of a hypotube.

3. The apparatus of claim 1, wherein the movement of the carriage is mediated via engagement with a threaded bar.

4. The apparatus of claim 3, wherein rotation of the threaded bar is controlled via a wheel.

5. The apparatus of claim 4, wherein the wheel is positioned at the distal end of the handle and the steering assembly is located proximally to the wheel.

6. The apparatus of claim 1, wherein the handle further comprises a delivery assembly and wherein the hollow needle is in fluid communication with the delivery assembly.

7. The apparatus of claim 6, wherein the delivery assembly is located at the proximal end of the handle.

8. The apparatus of claim 7, wherein the handle is configured such that the delivery assembly and the steering assembly are placed in a substantially linear arrangement along a central axis of the handle.

9. The apparatus of claim 6, wherein the delivery assembly is arranged to facilitate delivery of a pharmaceutical composition.

10. The apparatus of claim 6, wherein the delivery assembly is arranged to facilitate delivery of a cellular preparation.

11. A percutaneous catheter comprising an apparatus as claimed in claim 1.

* * * * *